United States Patent
Janka et al.

(10) Patent No.: US 9,943,834 B2
(45) Date of Patent: *Apr. 17, 2018

(54) FURAN-2,5-DICARBOXYLIC ACID PURGE PROCESS

(71) Applicant: EASTMAN CHEMICAL COMPANY, Kingsport, TN (US)

(72) Inventors: Mesfin Janka, Kingsport, TN (US); Kenny Parker, Afton, TN (US); Ashfaq Shaikh, Kingsport, TN (US); Lee Partin, Kingsport, TN (US)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/317,692

(22) Filed: Jun. 27, 2014

(65) Prior Publication Data

US 2015/0322028 A1 Nov. 12, 2015

Related U.S. Application Data

(60) Provisional application No. 61/990,140, filed on May 8, 2014.

(51) Int. Cl.

| | |
|---|---|
| *B01J 27/32* | (2006.01) |
| *B01D 11/04* | (2006.01) |
| *B01D 17/00* | (2006.01) |
| *C07D 307/68* | (2006.01) |
| *B01J 10/00* | (2006.01) |
| *B01J 23/889* | (2006.01) |
| *B01J 27/128* | (2006.01) |
| *B01J 38/12* | (2006.01) |
| *B01J 35/12* | (2006.01) |

(52) U.S. Cl.
CPC ............ *B01J 27/32* (2013.01); *B01D 11/04* (2013.01); *B01D 11/0446* (2013.01); *B01D 17/00* (2013.01); *B01J 10/002* (2013.01); *B01J 23/8892* (2013.01); *B01J 27/128* (2013.01); *C07D 307/68* (2013.01); *B01J 35/12* (2013.01); *B01J 38/12* (2013.01); *Y02P 20/584* (2015.11)

(58) Field of Classification Search
CPC ....... C07D 307/68; B01J 27/32; B01J 27/128; B01J 10/002; B01J 23/8892; B01J 35/12; B01J 38/12; B01D 17/00; B01D 11/04; B01D 11/0446; Y02P 20/584
See application file for complete search history.

(56) References Cited

U.S. PATENT DOCUMENTS

| | | | |
|---|---|---|---|
| 2,797,197 A | 6/1957 | Thompson et al. | |
| 3,203,963 A | 8/1965 | Hales et al. | |
| 3,326,944 A | 6/1967 | Lew | |
| 4,356,319 A * | 10/1982 | Roffia | B01J 31/04 502/28 |
| 4,977,283 A | 12/1990 | Leupold et al. | |
| 6,737,481 B1 | 5/2004 | Kurian et al. | |
| 7,052,764 B2 | 5/2006 | Chang et al. | |
| 7,385,081 B1 | 6/2008 | Gong | |
| 7,411,078 B2 | 8/2008 | Miura et al. | |
| 7,572,925 B2 | 8/2009 | Dumesic et al. | |
| 7,700,788 B2 | 4/2010 | Lilga et al. | |
| 8,183,020 B2 | 5/2012 | Hanke | |
| 8,193,381 B2 | 6/2012 | Lilga et al. | |
| 8,193,382 B2 | 6/2012 | Lilga et al. | |
| 8,748,479 B2 | 6/2014 | Shaikh et al. | |
| 8,772,513 B2 | 7/2014 | Janka et al. | |
| 8,791,277 B2 | 7/2014 | Janka et al. | |
| 8,791,278 B2 | 7/2014 | Shaikh et al. | |
| 8,796,477 B2 | 8/2014 | Janka et al. | |
| 8,809,556 B2 | 8/2014 | Janka et al. | |
| 8,846,960 B2 | 9/2014 | Janka et al. | |
| 8,916,719 B2 | 12/2014 | Shaikh et al. | |
| 8,916,720 B2 | 12/2014 | Shaikh et al. | |
| 8,969,404 B2 | 3/2015 | Janka et al. | |
| 9,156,805 B2 | 10/2015 | Janka et al. | |
| 9,206,149 B2 | 12/2015 | Janka et al. | |
| 9,573,120 B2 | 2/2017 | Parker | |
| 2002/0193631 A1 | 12/2002 | Park et al. | |
| 2003/0055271 A1 | 3/2003 | Grushin et al. | |
| 2006/0205977 A1 | 9/2006 | Sumner, Jr. et al. | |

(Continued)

FOREIGN PATENT DOCUMENTS

| | | |
|---|---|---|
| EP | 87340 | 7/1959 |
| EP | 1 834 951 A1 | 9/2007 |

(Continued)

OTHER PUBLICATIONS

IUPAC 1993, 65, 2373 (Nomenclature for liquid-liquid distribution (solvent extraction) (IUPAC Recommendations 1993)) on p. 2388; http://www.iupac.org/goldbook/R05122.pdf; (2014); p. 1.*
Shah, Y. T., "Design parameters estimations for bubble column reactors." AIChE Journal 28.3 (1982): 353-379.*
Slavinskaya, V. A., et al., "Liquid-Phase Catalytic Oxidation of 5-Methylfurfural," React. Kinet. Catal. Lett., 1979, vol. 11, No. 3, pp. 215-220.
Gandini, A., et al., "Rapid Communication: The Furan Counterpart of Poly(ethylene terephthalate): An Alternative Material Based on Renewable Resources," Journal of Polymer Science: Part A: Polymer Chemistry, 2009, vol. 47, pp. 295-298, Wiley Periodicals, Inc.
Partenheimer, W. et al., "Synthesis of 2,5-Diformylfuran and Furan-2,5-Dicarboxylic Acid by Catalytic Air-Oxidation of 5-Hydroxymethylfurfural. Unexpectedly Selective Aerobic Oxidation of Benzyl Alcohol to Benzaldehyde with Metal/Bromide Catalysts," Adv. Synth. Catal., 2001, vol. 343, No. 1, pp. 102-111.

(Continued)

*Primary Examiner* — John M Mauro
(74) *Attorney, Agent, or Firm* — Steven A. Owen

(57) ABSTRACT

Disclosed is an oxidation process to produce a crude carboxylic acid product carboxylic acid product. The process comprises oxidizing a feed stream comprising at least one oxidizable compound to generate a crude carboxylic acid slurry comprising furan-2,5-dicarboxylic acid (FDCA) and compositions thereof. Also disclosed is a process to produce a dry purified carboxylic acid product by utilizing various purification methods on the crude carboxylic acid.

16 Claims, 2 Drawing Sheets

(56) References Cited

U.S. PATENT DOCUMENTS

| | | | |
|---|---|---|---|
| 2007/0232815 A1 | 10/2007 | Miura et al. |
| 2009/0124829 A1 | 5/2009 | Gong |
| 2009/0131690 A1 | 5/2009 | Gruter et al. |
| 2009/0156841 A1 | 6/2009 | Sanborn et al. |
| 2009/0326262 A1 | 12/2009 | Wan |
| 2010/0210867 A1 | 8/2010 | Bustamante et al. |
| 2011/0092720 A1 | 4/2011 | Yutaka et al. |
| 2012/0302768 A1 | 11/2012 | Janka et al. |
| 2012/0302769 A1 | 11/2012 | Janka et al. |
| 2012/0302770 A1 | 11/2012 | Janka et al. |
| 2012/0302771 A1 | 11/2012 | Janka et al. |
| 2012/0302772 A1 | 11/2012 | Shaikh et al. |
| 2012/0302773 A1 | 11/2012 | Janka et al. |
| 2013/0345452 A1 | 12/2013 | Janka et al. |
| 2014/0024844 A1 | 1/2014 | Janka et al. |
| 2014/0142328 A1 | 5/2014 | Shaikh et al. |
| 2014/0235880 A1 | 8/2014 | Shaikh et al. |
| 2014/0364633 A1 | 12/2014 | Janka et al. |
| 2015/0321119 A1 | 11/2015 | Parker et al. |
| 2015/0322029 A1 | 11/2015 | Janka et al. |
| 2016/0221980 A1 | 8/2016 | Parker et al. |
| 2016/0311790 A1 | 10/2016 | Janka et al. |
| 2016/0332979 A1 | 11/2016 | Fontenot et al. |
| 2017/0137396 A1 | 5/2017 | Mihovilovic |

FOREIGN PATENT DOCUMENTS

| | | |
|---|---|---|
| EP | 2 197 868 B1 | 4/2011 |
| EP | 2 197 865 B1 | 8/2012 |
| JP | 2007-261986 A | 10/2007 |
| JP | 2007-261990 A | 10/2007 |
| JP | 2009-001519 A | 1/2009 |
| JP | 2009-013079 A | 1/2009 |
| JP | 2009-242312 A | 10/2009 |
| SU | 162962 A | 9/1962 |
| WO | WO 02/098836 A1 | 12/2002 |
| WO | WO 2007/092183 A2 | 8/2007 |
| WO | WO 2008/054804 A2 | 5/2008 |
| WO | WO 2009/023174 A2 | 2/2009 |
| WO | WO 2009/030506 A4 | 3/2009 |
| WO | WO 2009/030507 A4 | 3/2009 |
| WO | WO 2010/077133 A1 | 7/2010 |
| WO | WO 2010/132740 A2 | 11/2010 |
| WO | WO 2011/043660 A2 | 4/2011 |
| WO | WO 2012/161968 A1 | 11/2012 |
| WO | WO 2014/193634 A1 | 12/2014 |
| WO | WO 2014/197195 A2 | 12/2014 |

OTHER PUBLICATIONS

Lewkowski, J.; "Synthesis, Chemistry and Applications of 5-Hydroxymethylfurfural and its Derivatives," ARKIVOC, 2001, pp. 17-54.

Zakharov, I. V., "Mechanism of Initiation and Inhibition by Mn(II) in Hydrocarbon Oxidation in the Presence a Cobalt—Manganese Bromide Catalyst," Kinetics and Catalysis, 1998, vol. 39, No. 4, pp. 485-492.

Jiao, X. J. et al., "Kinetics of Manganese(III) Acetate in Acetic Acid: Generation of Mn(III) with Co(III), Ce(IV), and Dibromide Radicals; Reactions of Mn(III) with Mn(II), Co(II), Hydrogen Bromide, and Alkali Bromides," Inorg. Chem., 2000, vol. 39, pp. 1549-1554, American Chemical Society.

Copending U.S. Appl. No. 13/228,816, filed Sep. 9, 2011, Mesfin Ejerssa Janka, et al.

Copending U.S. Appl. No. 13/228,799, filed Sep. 9, 2011, Mesfin Ejerssa Janka, et al.

Copending U.S. Appl. No. 13/228,809, filed Sep. 9, 2011, Mesfin Ejerssa Janka, et al.

Copending U.S. Appl. No. 13/228,803, filed Sep. 9, 2011, Mesfin Ejerssa Janka, et al.

Copending U.S. Appl. No. 13/228,797, filed Sep. 9, 2011, Mesfin Ejerssa Janka, et al.

Copending U.S. Appl. No. 13/228,813, filed Sep. 9, 2011, Ashfaq Shaikh, et al.

PCT International Search Report and Written Opinion dated Jul. 27, 2012 for International Application No. PCT/US2012/037223.

PCT International Search Report and Written Opinion dated Aug. 7, 2012 for International Application No. PCT/US2012/037218.

PCT International Search Report and Written Opinion dated Jul. 27, 2012 for International Application No. PCT/US2012/037204.

PCT International Search Report and Written Opinion dated Jul. 27, 2012 for International Application No. PCT/US2012/037206.

PCT International Search Report and Written Opinion dated Aug. 3, 2012 for International Application No. PCT/US2012/037210.

Copending U.S. Appl. No. 13/553,976, filed Jul. 20, 2012, Mesfin Ejerssa Janka, et al.

PCT International Search Report and Written Opinion dated Aug. 23, 2012 for International Application No. PCT/US2012/037228.

Chheda et al., "Production of 5-hydromethylfurfural and furfural by dehydration of biomass-derived mono- and poly-saccharides." Green Chemistry, vol. 9, pp. 342-350 (2007).

Werpy et al., "Top Value Added Chemicals from Biomass" DOE (Pacific NW National Laboratory) (Aug. 2004).

Verevkin et al., "Biomass-Derived Platform Chemicals: Thermodynamic Studies on the Conversion of 5-Hydroxymethylfurfural into Bulk Intermediates" Ind. Eng. Chem. Res., vol. 48, pp. 10087-10093 (2009).

Manasek, Z., "Modification of a Fiber-Forming Polyester Based on 2,5-Furandicarboxylic Acid", Mar. 20, 1963, pp. 35-38, UDC 677.465.

Rodivilova et al., "Synthesis and Investigation of Polyarylates Based on 2,5-Furandicarboxylic Acid and Diphenylolpropane", Khimiya I Khimicheskaya Tekhnologiya, No. 7, 1968, pp. 818-821.

Copending U.S. Appl. No. 13/758,070, filed Feb. 4, 2013, Kenny Randolph Parker, et al.

Copending U.S. Appl. No. 13/758,080, filed Feb. 4, 2013, Mesfin Ejerssa Janka, et al.

Office Action dated Apr. 18, 2013 received in co-pending U.S. Appl. No. 13/228,797.

Office Action dated Apr. 18, 2013 received in co-pending U.S. Appl. No. 13/228,813.

Office Action dated Apr. 29, 2013 received in co-pending U.S. Appl. No. 13/228,799.

Office Action dated May 31, 2013 received in co-pending U.S. Appl. No. 13/228,803.

Office Action dated Jun. 6, 2013 received in co-pending U.S. Appl. No. 13/228,809.

Office Action dated Jun. 6, 2013 received in co-pending U.S. Appl. No. 13/228,816.

PCT International Search Report and Written Opinion dated Jul. 29, 2013 for International Application No. PCT/US2013/044935.

PCT International Search Report and Written Opinion dated Aug. 9, 2013 for International Application No. PCT/US2013/044932.

Office Action dated Sep. 30, 2013 received in co-pending U.S. Appl. No. 13/758,070.

Office Action dated Sep. 30, 2013 received in co-pending U.S. Appl. No. 13/758,080.

Moldenhauer, et al., "Beitrage zur Furanchemie I", Justus Liebigs Annalen Der Chemie, vol. 580, 1953, pp. 169-190.

Office Action dated Oct. 25, 2013 received in co-pending U.S. Appl. No. 13/228,813.

PCT International Search Report and Written Opinion dated Oct. 31, 2013 for International Application No. PCT/US2013/050799.

Office Action dated Nov. 5, 2013 received in co-pending U.S. Appl. No. 13/228,797.

Office Action dated Nov. 8, 2013 received in co-pending U.S. Appl. No. 13/228,803.

Office Action dated Nov. 8, 2013 received in co-pending U.S. Appl. No. 13/758,070.

Office Action dated Nov. 12, 2013 received in co-pending U.S. Appl. No. 13/228,799.

Office Action dated Nov. 14, 2013 received in co-pending U.S. Appl. No. 13/228,809.

Office Action dated Nov. 18, 2013 received in co-pending U.S. Appl. No. 13/758,088.

(56) References Cited

OTHER PUBLICATIONS

Copending U.S. Appl. No. 14/084,165, filed Nov. 19, 2013, Ashfaq Shaikh et al.
PCT International Search Report and Written Opinion dated Nov. 28, 2013 for International Application No. PCT/US2013/050794.
Office Action dated Dec. 13, 2013 received in co-pending U.S. Appl. No. 13/228,816.
Office Action dated Dec. 16, 2013 received in co-pending U.S. Appl. No. 13/553,976.
Notice of Allowance dated Apr. 1, 2014 received in co-pending U.S. Appl. No. 13/758,080.
Notice of Allowance dated Apr. 1, 2014 received in co-pending U.S. Appl. No. 13/758,070.
Office Action dated Apr. 17, 2014 received in co-pending U.S. Appl. No. 13/758,072.
Copending U.S. Appl. No. 14/259,754, filed Apr. 23, 2014, Ashfaq Shaikh et al.
Notice of Allowance dated May 13, 2014 received in co-pending U.S. Appl. No. 13/758,088.
Copending U.S. Appl. No. 14/282,360, filed May 20, 2014, Janka et al.
Office Action dated Apr. 25, 2014 received in co-pending U.S. Appl. No. 13/228,797.
Office Action dated Apr. 25, 2014 received in co-pending U.S. Appl. No. 13/228,809.
Notice of Allowance dated Apr. 28, 2014 received in co-pending U.S. Appl. No. 13/228,803.
Notice of Allowance dated Apr. 28, 2014 received in co-pending U.S. Appl. No. 13/228,813.
Office Action dated Apr. 30, 2014 received in co-pending U.S. Appl. No. 13/798,235.
Notice of Allowance dated May 1, 2014 received in co-pending U.S. Appl. No. 13/228,799.
Office Action dated May 29, 2014 received in co-pending U.S. Appl. No. 13/228,816.
PCT International Search Report and Written Opinion dated Dec. 30, 2013 for International Application No. PCT/US2013/056362.
Office Action dated Sep. 26, 2014, 2014 received in co-pending U.S. Appl. No. 13/758,072.
Notice of Allowance dated Dec. 17, 2014 received in co-pending U.S. Appl. No. 13/758,080.
Office Action dated Apr. 25, 2014 received in co-pending U.S. Appl. No. 13/798,257.
Notice of Allowance dated Jun. 11, 2014 received in co-pending U.S. Appl. No. 13/553,976.
Copending U.S. Appl. No. 14/309,010, filed Jun. 19, 2014, Janka et al.
Copending U.S. Appl. No. 14/317,588, filed Jun. 27, 2014, Parker et al.
Copending U.S. Appl. No. 14/317,782, filed Jun. 27, 2014, Parker et al.
Copending U.S. Appl. No. 14/317,875, filed Jun. 27, 2014, Janka et al.
Office Action dated May 22, 2015received in co-pending U.S. Appl. No. 14/317,875.
Office Action dated Aug. 3, 2015 received in co-pending U.S. Appl. No. 14/317,782.
Office Action dated Feb. 10, 2016 received in co-pending U.S. Appl. No. 14/317,588.
Office Action dated Mar. 18, 2016 received in co-pending U.S. Appl. No. 14/317,875.
Copending U.S. Appl. No. 15/096,584, filed Apr. 12, 2016, Kenny Randolph Parker, et al.
Notice of Allowance dated Apr. 15, 2016 received in co-pending U.S. Appl. No. 14/317,782.
PCT International Search Report and Written Opinion dated Aug. 19, 2015 for International Application No. PCT/US2015/029381.
Copending U.S. Appl. No. 15/096,584, filed Apr. 12, 2016, Kenny Randolph Parker, et al., now publication No. 2016-0221980.
Co-pending U.S. Appl. No. 15/200,467, filed Jul. 1, 2016; Janka et al. now publication No. 2016-0311790.
Notice of Allowance dated Jul. 14, 2016 received in co-pending U.S. Appl. No. 14/317,588.
Copending U.S. Appl. No. 15/217,319, filed Jul. 22, 2016, Kevin John Fontenot, et al. now publication No. 2016-0332979.
Notice of Allowance dated Oct. 7, 2016 received in co-pending U.S. Appl. No. 14/317,875.
Notice of Allowance dated Nov. 23, 2016 received in co-pending U.S. Appl. No. 14/317,588.
Notice of Allowance dated Dec. 6, 2016 received in co-pending U.S. Appl. No. 14/317,782.
Co-pending U.S. Appl. No. 15/435,362, filed Feb. 17, 2017; Parker et al.
Office Action dated Sep. 14, 2017 received in co-pending U.S. Appl. No. 15/200,467.
Office Action dated Oct. 13, 2017 received in co-pending U.S. Appl. No. 15/217,319.
Office Action dated Jun. 7, 2017 received in co-pending U.S. Appl. No. 15/096,584.

\* cited by examiner

FURAN-2,5-DICARBOXYLIC ACID PURGE PROCESS

CROSS REFERENCE TO RELATED APPLICATION(S)

This Application claims the benefit of U.S. Provisional Patent Application Ser. No. 61/990,140 filed May 8, 2014, the entire disclosure of which is incorporated by reference herein.

BACKGROUND OF THE INVENTION

Aromatic dicarboxylic acids such as terephthalic acid and isophthalic acid or their di-esters, dimethyl terephthalate as for example, are used to produce a variety of polyester products, important examples of which are poly(ethylene terephthalate) and its copolymers. The aromatic dicarboxylic acids are synthesized by the catalytic oxidation of the corresponding dialkyl aromatic compounds which are obtained from fossil fuels (US 2006/0205977 A1). Esterification of these diacids using excess alcohol produces the corresponding di-esters (US2010/0210867A1). There is a growing interest in the use of renewable resources as feed stocks for the chemical industries mainly due to the progressive reduction of fossil reserves and their related environmental impacts.

Furan-2,5-dicarboxylic acid (FDCA) is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) (Gandini, A.; Silvestre, A. J; Neto, C. P.; Sousa, A. F.; Gomes, M., *J. Poly. Sci. A* 2009, 47, 295). FDCA has been prepared by oxidation of 5-(hydroxymethyl) furfural (5-HMF) under air using homogenous catalysts (US2003/0055271 A1 and Partenheimer, W.; Grushin, V. V., *Adv. Synth. Catal.* 2001, 343, 102-111.) but only a maximum of 44.8% yield using a Co/Mn/Br catalyst system and a maximum of 60.9% yield was reported using Co/Mn/Br/Zr catalysts combination. Recently, we reported a process for producing furan-2,5-dicarboxylic acid (FDCA) in high yields by liquid phase oxidation of 5-HMF or its derivatives using a Co/Mn/Br catalyst system that minimizes solvent and starting material loss through carbon burn (U.S. patent application Ser. Nos. 13/228,803, 13/228,809, 13/228,816, and 13/228,799, herein incorporated by reference).

Disclosed is a method for recovering a portion of oxidation solvent, a portion of oxidation catalyst, and removing a portion of oxidation by-products and raw material impurities from a solvent stream generated in a process to make furan-2,5-dicarboxylic acid (FDCA). The process comprises oxidizing a feed stream comprising at least one oxidizable compound selected from the following group: 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters and mixed feed-stocks of 5-HMF and 5-HMF ethers and mixed feed-stocks of 5-HMF and 5-alkyl furfurals to generate a crude carboxylic acid slurry comprising furan-2,5-dicarboxylic acid (FDCA) in an oxidation zone, cooling a crude carboxylic acid slurry in a cooling zone to generate a cooled crude carboxylic acid slurry, removing impurities from a cooled crude carboxylic acid slurry in a solid-liquid separation zone to form a low impurity carboxylic acid stream and a mother liquor stream, routing at least a portion of the mother liquor stream to a mother liquor purge zone to generate a recycle oxidation solvent stream, a recycle catalyst rich stream, a raffinate stream, and an impurity rich waste stream.

DETAILED DESCRIPTION

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

Figure 1:
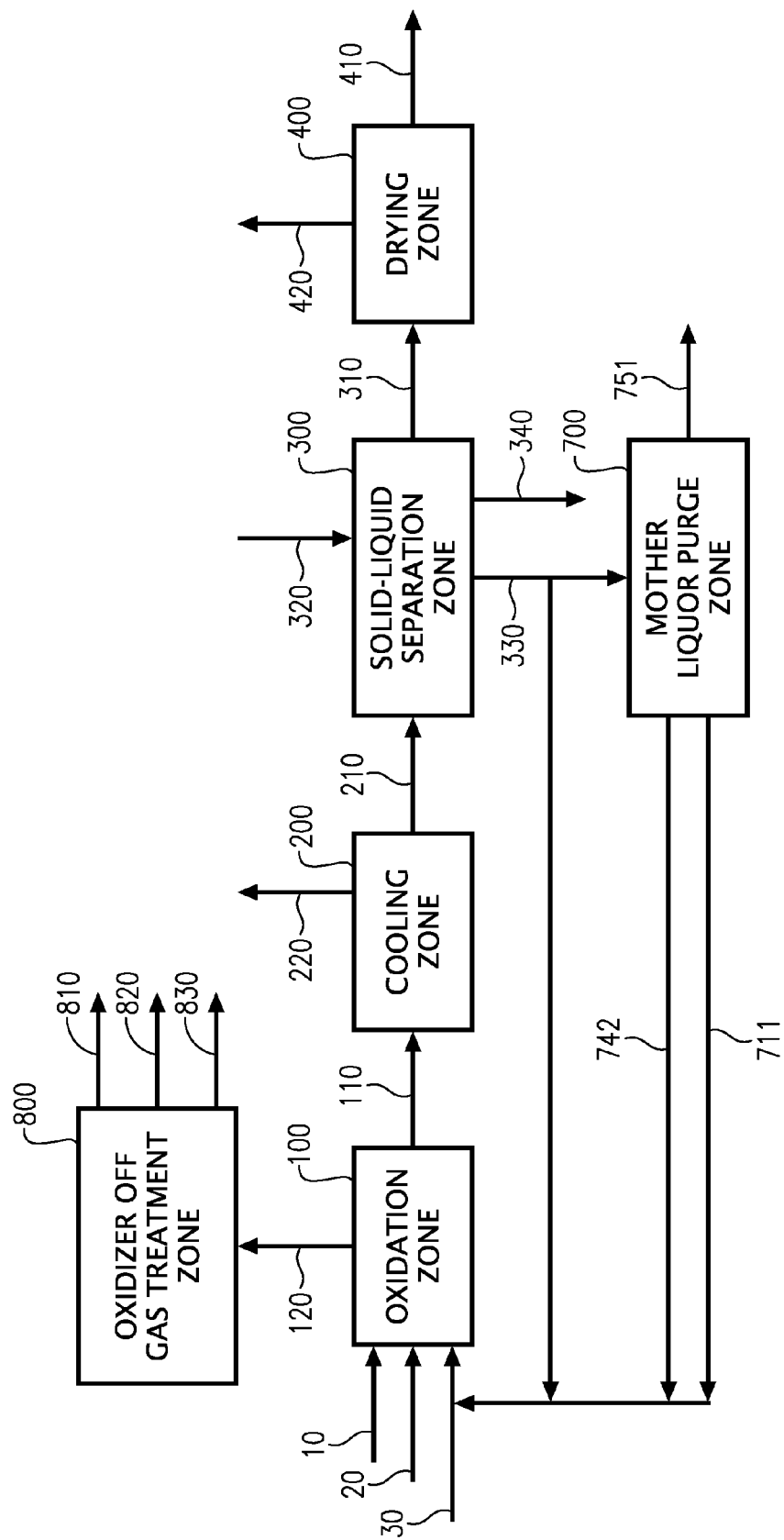
FIG. 1 illustrates different embodiments of the invention wherein a process to produce a dried carboxylic acid 410 is provided.
Figure 2:
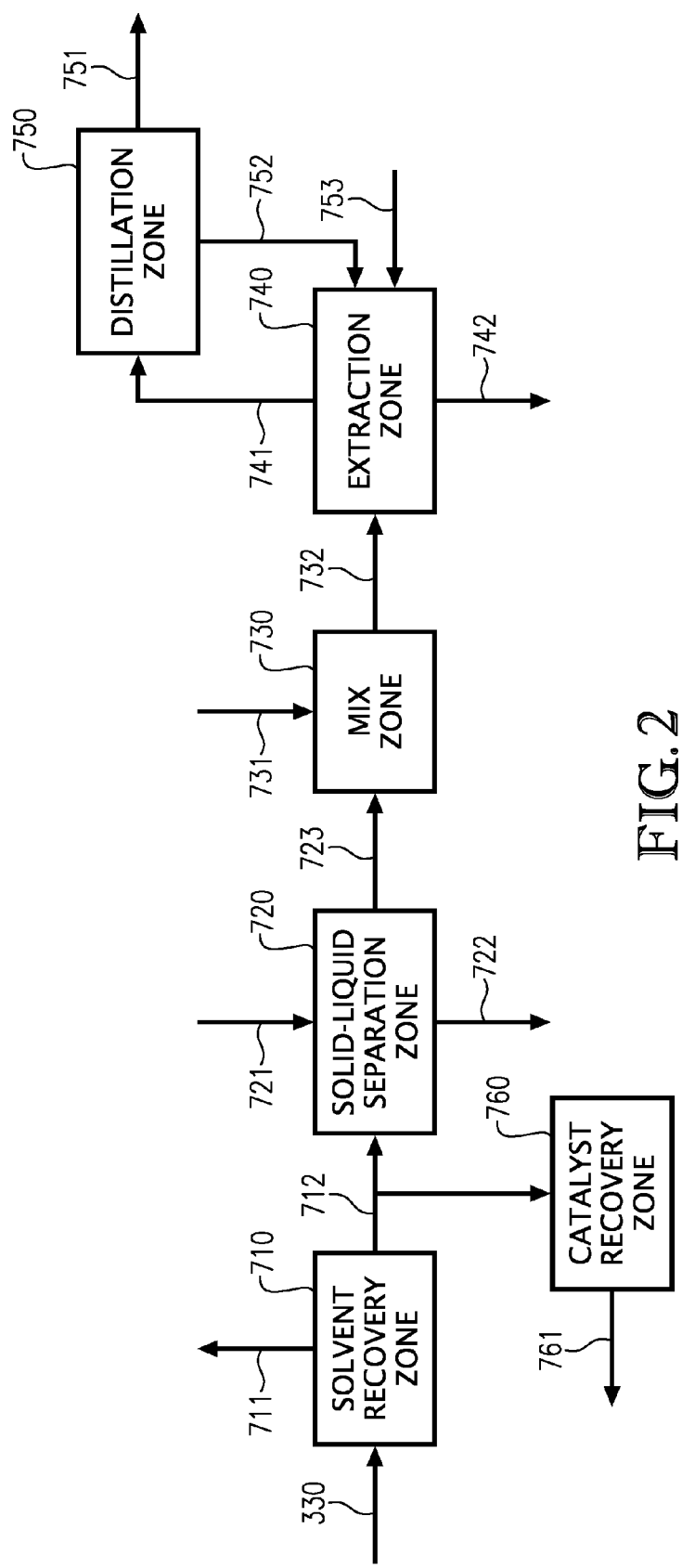
FIG. 2 illustrates an embodiment of the invention, wherein an purge stream is created. This figure is a detailed illustration on zone 700 in FIG. 1.

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively One embodiment of the present invention is illustrated in FIGS. 1 and 2. The present invention provides a process for recovering a portion of oxidation solvent, a portion of oxidation catalyst, and removing a portion of oxidation by-products and raw material impurities from a solvent stream generated in a process to make furan-2,5-dicarboxylic acid (FDCA).:

Step (a) comprises feeding oxidation solvent, a catalyst system, a gas stream comprising oxygen, and oxidizable raw material comprising at least one compound selected from the group of formula: 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters, mixed feed-stocks of 5-HMF and 5-HMF ethers, and mixed feed-stocks of 5-HMF and 5-alkyl furfurals to an oxidation zone 100 to generate a crude carboxylic acid slurry 110 comprising furan-2,5-dicarboxylic (FDCA).

Structures for the preferred oxidizable raw material compounds are outlined below:

Preferred 5-HMF Derivative Feeds

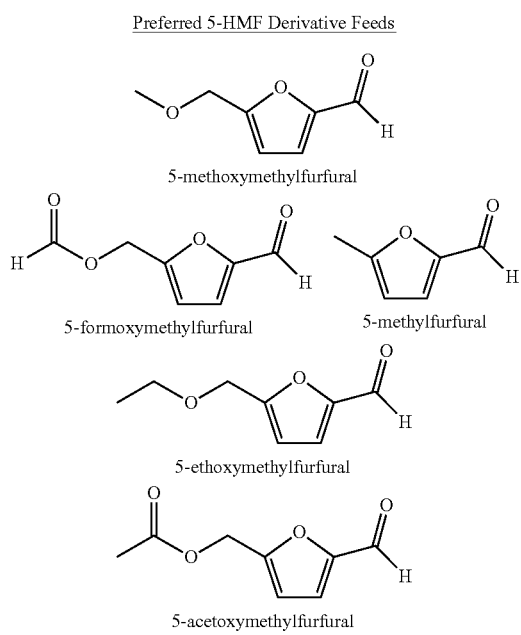

-continued

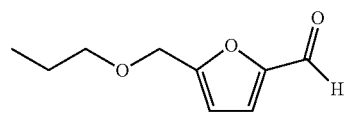

5-propoxymethylfurfural

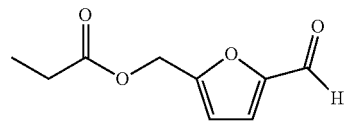

5-propionoxymethylfurfural

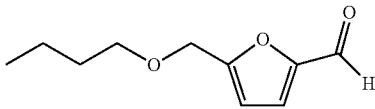

5-butoxymethylfurfural

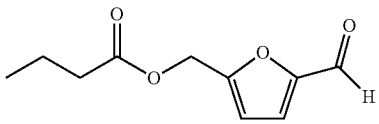

5-butyroxymethylfurfural

5-HMF feed is oxidized with elemental O$_2$ in a multi-step reaction to form FDCA with 5-formyl furan-2-carboxylic acid (FFCA) as a key intermediate (Eq 1). Oxidation of 5-(acetoxymethyl)furfural (5-AMF), which contains an oxidizable ester and aldehydes moieties, produces FDCA, FFCA, and acetic acid (Eq 2). Similarly, oxidation of 5-(ethoxymethyl)furfural (5-EMF) produces FDCA, FFCA, 5-(ethoxycarbonyl)furan-2-carboxylic acid (EFCA) and acetic acid (Eq 3).

(1)

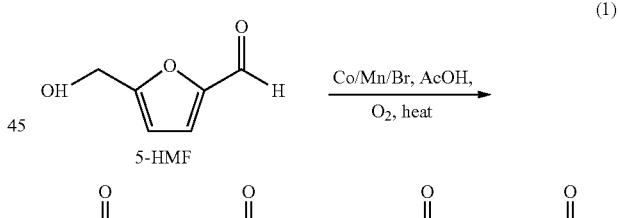

(2)

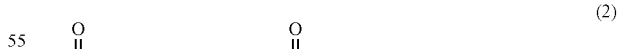

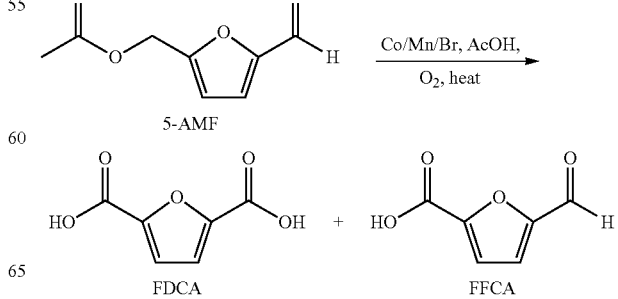

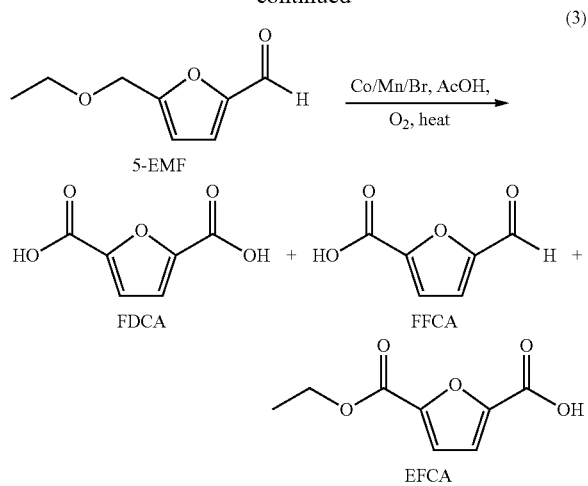

(3)

Streams routed to the primary oxidation zone 100 comprise gas stream 10 comprising oxygen, and stream 30 comprising oxidation solvent, and stream 20 comprising oxidizable raw material. In another embodiment, streams routed to the oxidization zone 100 comprise gas stream 10 comprising oxygen and stream 20 comprising oxidation solvent, catalyst, and oxidizable raw material. In yet another embodiment, the oxidation solvent, gas comprising oxygen, catalyst system, and oxidizable raw materials can be fed to the oxidization zone 100 as separate and individual streams or combined in any combination prior to entering the oxidization zone 100 wherein said feed streams may enter at a single location or in multiple locations into oxidizer zone 100.

Suitable catalyst systems is at least one compound selected from, but are not limited to, cobalt, bromine, and manganese compounds, which are soluble in the selected oxidation solvent. The preferred catalyst system comprises cobalt, manganese and bromine wherein the weight ratio of cobalt to manganese in the reaction mixture is from about 10 to about 400 and the weight ratio of cobalt to bromine is from about 0.7 to about 3.5. Data shown in Tables 1 to 3 demonstrate that very high yield of FDCA can be obtained using 5-HMF or its derivatives using the catalyst composition described above.

Suitable oxidation solvents include, but are not limited to, aliphatic mono-carboxylic acids, preferably containing 2 to 6 carbon atoms, and mixtures thereof, and mixtures of these compounds with water. In one embodiment, the oxidation solvent comprises acetic acid wherein the weight % of acetic acid in the oxidation solvent is greater than 50%, greater than 75%, greater than 85%, and greater than 90%. In another embodiment, the oxidation solvent comprises acetic acid and water wherein the proportions of acetic acid to water is greater than 1:1, greater than 6:1, greater than 7:1, greater than 8:1, and greater than 9:1.

The temperature in oxidation zone can range from 100° C. to 220° C., or 100° C. to 200° C., or 130° C. to 180° C., or 100° C. to 180° C. and can preferably range from 110° C. to 160° C. In another embodiment, the temperature in oxidation zone can range from 105° C. to 140° C.

One advantage of the disclosed oxidation conditions is low carbon burn as illustrated in Tables 1 to 3. Oxidizer off gas stream 120 is routed to the oxidizer off gas treatment zone 800 to generate an inert gas stream 810, liquid stream 820 comprising water, and a recovered oxidation solvent stream 830 comprising condensed solvent. In one embodiment, at least a portion of recovered oxidation solvent stream 830 is routed to wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process. In another embodiment, at least a portion of the energy in stream 120 is recovered in the form of steam and or electricity.

In another embodiment of the invention, a process is provided for producing furan-2,5-dicarboxylic acid (FDCA) in high yields by liquid phase oxidation that minimizes solvent and starting material loss through carbon burn. The process comprises oxidizing at least one oxidizable compound in an oxidizable raw material stream 30 in the presence of an oxidizing gas stream 10, oxidation solvent stream 20, and at least one catalyst system in a oxidation zone 100; wherein the oxidizable compound is 5-(hydroxymethyl)furfural (5-HMF); wherein the solvent stream comprises acetic acid with or without the presence of water; wherein the catalyst system comprising cobalt, manganese, and bromine, wherein the weight ratio of cobalt to manganese in the reaction mixture is from about 10 to about 400. In this process, the temperature can vary from about 100° C. to about 220° C., from about 105° C. to about 180° C., and from about 110° C. to about 160° C. The cobalt concentration of the catalyst system can range from about 1000 ppm to about 6000 ppm, and the amount of manganese can range from about 2 ppm to about 600 ppm, and the amount of bromine can range from about 300 ppm to about 4500 ppm with respect to the total weight of the liquid in the reaction medium.

Step (b) comprises routing the crude carboxylic acid slurry 110 comprising FDCA to cooling zone 200 to generate a cooled crude carboxylic acid slurry stream 210 and a $1^{st}$ vapor stream 220 comprising oxidation solvent vapor. The cooling of crude carboxylic slurry stream 110 can be accomplished by any means known in the art. Typically, the cooling zone 200 comprises a flash tank. In another embodiment, a portion up to 100% of the crude carboxylic acid slurry stream 110 is routed directly to solid-liquid separation zone 300, thus said portion up to 100% is not subjected to cooling in cooling zone 200. The temperature of stream 210 can range from 35° C. to 210° C., 55° C. to 120° C., and preferably from 75° C. to 95° C.

Step (c) comprises isolating, washing, and dewatering solids present in the cooled crude carboxylic acid slurry stream 210 in the solid-liquid separation zone 300 to generate a crude carboxylic acid wet cake stream 310 comprising FDCA. These functions may be accomplished in a single solid-liquid separation device or multiple solid-liquid separation devices. The solid-liquid separation zone comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %.

Equipment suitable for the solid liquid separation zone can typically be at least one of the following types of devices: centrifuge, cyclone, rotary drum filter, belt filter, pressure leaf filter, candle filter, and the like. The preferred solid liquid separation device for the solid liquid separation zone is a rotary pressure drum filter.

The temperature of cooled crude carboxylic acid slurry steam 210 which is routed to the solid-liquid separation zone 300 can range from 35° C. to 210° C., 55° C. to 120° C., and is preferably from 75° C. to 95° C. Wash solvent stream 320 comprises a liquid suitable for displacing and washing mother liquor from the solids. In one embodiment, a suitable wash solvent comprises acetic acid. In another embodiment, a suitable wash solvent comprises acetic acid and water. In yet another embodiment, a suitable wash solvent comprises water and can be 100% water. The temperature of the wash solvent can range from 20° C. to 160° C., 40° C. to 110° C., and preferably from 50° C. to 90° C.

The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3. After solids are washed in the solid liquid separation zone, they are dewatered. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310 comprising FDCA.

In one embodiment, dewatering is accomplished in a filter by passing a stream comprising gas through the solids to displace free liquid after the solids have been washed with a wash solvent. In an embodiment, dewatering of the wet cake solids in solid-liquid separation zone 300 can be implemented before washing and after washing the wet cake solids in zone 300 to minimize the amount of oxidizer solvent present in the wash liquor stream 340. In another embodiment, dewatering is achieved by centrifugal forces in a perforated bowl or solid bowl centrifuge.

The mother liquor steam 330 generated in solid-liquid separation zone 300 comprises oxidation solvent, catalyst, and impurities. From 5 wt % to 95 wt %, from 30 wt % to 90 wt %, and most preferably from 40 wt % to 80 wt % of mother liquor present in the crude carboxylic acid slurry 110 is isolated in solid-liquid separation zone 300 to generate mother liquor stream 330 resulting in dissolved matter comprising impurities present in mother liquor stream 330 not going forward in the process.

In one embodiment, a portion of mother liquor stream 330 is routed to a mother liquor purge zone 700, wherein a portion is at least 5 weight %, at least 25 weight %, at least 45 weight %, at least 55 weight % at least 75 weight %, or at least 90 weight %. In another embodiment, at least a portion of the mother liquor stream 330 is routed back to the oxidation zone 100, wherein a portion is at least 5 weight %. In yet another embodiment, at least a portion of mother liquor stream 330 is routed to a mother liquor purge zone 700 and to the oxidation zone 100 wherein a portion is at least 5 weight %. In one embodiment, the mother liquor purge zone 700 comprises an evaporative step to separate oxidation solvent from stream 330 by evaporation. Solids can be present in mother liquor stream 330 ranging from about 5 weight % to about 0.5 weight %. In yet another embodiment, any portion of mother liquor stream 330 routed to a mother liquor purge zone is first subjected to a solid liquid separation device to control solids present in stream 330 to less than 1 wt %, less than 0.5 wt %, less than 0.3 wt %, or less than 0.1% by weight. Suitable solid liquid separation equipment comprise a disc stack centrifuge and batch pressure filtration solid liquid separation devices. A preferred solid liquid separation device for this application comprises a batch candle filter.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream is routed to mother liquor purge zone 700 wherein a portion is at least 5 weight %. In another embodiment, at least a portion of wash liquor stream 340 is routed to oxidation zone 100 and mother liquor purge zone 700 wherein a portion is at least 5 weight %.

In another embodiment, at least a portion of the crude carboxylic acid slurry stream 110 up to 100 weight % is routed directly to the solid-liquid separation zone 300, thus this portion will bypass the cooling zone 200. In this embodiment, feed to the solid-liquid separation zone 300 comprises at least a portion of the crude carboxylic acid slurry stream 110 and wash solvent stream 320 to generate a crude carboxylic acid wet cake stream 310 comprising FDCA. Solids in the feed slurry are isolated, washed, and dewatered in solid-liquid separation zone 300. These functions may be accomplished in a single solid-liquid separation device or multiple solid-liquid separation devices. The solid-liquid separation zone comprises at least one solid-liquid separation device capable of separating solids and liquids, washing solids with a wash solvent stream 320, and reducing the % moisture in the washed solids to less than 30 weight %, less than 20 weight %, less than 15 weight %, and preferably less than 10 weight %. Equipment suitable for the solid liquid separation zone can typically be at least one of the following types of devices: centrifuge, cyclone, rotary drum filter, belt filter, pressure leaf filter, candle filter, and the like. The preferred solid liquid separation device for the solid liquid separation zone 300 is a continuous rotary pressure drum filter. The temperature of the crude carboxylic acid slurry stream, which is routed to the solid-liquid separation zone 300 can range from 40° C. to 210° C., 60° C. to 170° C., ° C. and is preferably from 80° C. to 160° C. The wash stream 320 comprises a liquid suitable for displacing and washing mother liquor from the solids. In one embodiment, a suitable wash solvent comprises acetic acid and water. In another embodiment, a suitable wash solvent comprises water up to 100% water. The temperature of the wash solvent can range from 20° C. to 180° C., 40° C. and 150° C., and preferably from 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone, they are dewatered. Dewatering involves reducing the mass of moisture present with the solids to less than 30% by weight, less than 25% by weight, less than 20% by weight, and most preferably less than 15% by weight resulting in the generation of a crude carboxylic acid wet cake stream 310. In one embodiment, dewatering is accomplished in a filter by passing a gas stream through the solids to displace free liquid after the solids have been washed with a wash solvent. In another embodiment, the dewatering of the wet cake in solid-liquid separation zone 300 can be implemented before washing and after washing the solids in zone 300 to minimize the amount of oxidizer solvent present in the wash liquor stream 340 by any method known in the art. In yet another embodiment, dewatering is achieved by centrifugal forces in a perforated bowl or solid bowl centrifuge.

Mother liquor steam 330 generated in the solid-liquid separation zone 300 comprising oxidation solvent, catalyst, and impurities. From 5 wt % to 95 wt %, from 30 wt % to 90 wt %, and most preferably from 40 wt % to 80 wt % of mother liquor present in the crude carboxylic acid slurry stream 110 is isolated in solid-liquid separation zone 300 to generate mother liquor stream 330 resulting in dissolved matter comprising impurities present in mother liquor stream 330 not going forward in the process. In one embodiment, a portion of mother liquor stream 330 is routed to a mother liquor purge zone 700, wherein a portion is at least 5 weight %, at least 25 weight %, at least 45 weight %, at least 55 weight % at least 75 weight %, or at least 90 weight %. In another embodiment, at least a portion is routed back to the oxidation zone 100, wherein a portion is at least 5 weight %. In yet another embodiment, at least a portion of mother liquor stream 330 is routed to a mother liquor purge zone and to the oxidation zone 100 wherein a portion is at least 5 weight %. In one embodiment, mother liquor purge zone 700 comprises an evaporative step to separate oxidation solvent from stream 330 by evaporation.

Wash liquor stream 340 is generated in the solid-liquid separation zone 300 and comprises a portion of the mother liquor present in stream 210 and wash solvent wherein the ratio of mother liquor mass to wash solvent mass is less than 3 and preferably less than 2. In an embodiment, at least a portion of wash liquor stream 340 is routed to oxidation zone 100 wherein a portion is at least 5 weight %. In an embodiment, at least a portion of wash liquor stream 340 is routed to mother liquor purge zone 700 wherein a portion is at least 5 weight %. In another embodiment, at least a portion of wash liquor stream is routed to oxidation zone 100 and mother liquor purge zone 700 wherein a portion is at least 5 weight %.

Mother liquor stream 330 comprises oxidation solvent, catalyst, soluble intermediates, and soluble impurities. It is desirable to recycle directly or indirectly at least a portion of the catalyst and oxidation solvent present in mother liquor stream 330 back to oxidation zone 100 wherein a portion is at least 5% by weight, at least 25%, at least 45%, at least 65%, at least 85%, or at least 95%. Direct recycling at least a portion of the catalyst and oxidation solvent present in mother liquor stream 330 comprises directly routing a portion of stream 330 to oxidizer zone 100. Indirect recycling at least a portion of the catalyst and oxidation solvent present in mother liquor stream 330 to oxidation zone 100 comprises routing at least a portion of stream 330 to at least one intermediate zone wherein stream 330 is treated to generate a stream or multiple streams comprising oxidation solvent and or catalyst that are routed to oxidation zone 100.

Step (d) comprises separating components of mother liquor stream 330 in mother liquor purge zone 700 for recycle to the process while also isolating those components not to be recycled comprising impurities. Impurities in stream 330 can originate from one or multiple sources. In an embodiment of the invention, impurities in stream 330 comprise impurities introduced into the process by feeding streams to oxidation zone 100 that comprise impurities. Mother liquor impurities comprise at least one impurity selected from the following group: 2,5-diformylfuran in an amount ranging from about 5 ppm to 800 ppm, 20 ppm to about 1500 ppm, 100 ppm to about 5000 ppm, 150 ppm to about 2.0 wt %; levulinic acid in an amount ranging from about 5 ppm to 800 ppm, 20 ppm to about 1500 ppm, 100 ppm to about 5000 ppm, 150 ppm to about 2.0 wt %; succinic acid in an amount ranging from about 5 ppm to 800 ppm, 20 ppm to about 1500 ppm, 100 ppm to about 5000 ppm, 150 ppm to about 2.0 wt %; acetoxy acetic acid in an amount ranging from about 5 ppm to 800 ppm, 20 ppm to about 1500 ppm, 100 ppm to about 5000 ppm, 150 ppm to about 2.0 wt %

An impurity is defined as any molecule not required for the proper operation of oxidation zone 100. For example, oxidation solvent, a catalyst system, a gas comprising oxygen, and oxidizable raw material comprising at least one compound selected from the group of formula: 5-(hydroxymethyl)furfural (5-HMF), 5-HMF esters (5-R(CO)OCH$_2$-furfural where R=alkyl, cycloalkyl and aryl), 5-HMF ethers (5-R'OCH$_2$-furfural, where R'=alkyl, cycloalkyl and aryl), 5-alkyl furfurals (5-R"-furfural, where R"=alkyl, cycloalkyl and aryl), mixed feed-stocks of 5-HMF and 5-HMF esters, mixed feed-stocks of 5-HMF and 5-HMF ethers, and mixed feed-stocks of 5-HMF and 5-alkyl furfurals are molecules required for the proper operation of oxidation zone 100 and are not considered impurities. Also, chemical intermediates formed in oxidation zone 100 that lead to or contribute to chemical reactions that lead to desired products are not considered impurities. Oxidation by-products that do not lead to desired products are defined as impurities. Impurities may enter oxidation zone 100 through recycle streams routed to the oxidation zone 100 or by impure raw material streams fed to oxidation zone 100.

In one embodiment, it is desirable to isolate a portion of the impurities from oxidizer mother liquor stream 330 and purge or remove them from the process as purge stream 751. In an embodiment of the invention, from 5 to 100% by weight, of mother liquor stream 330 generated in solid-liquid separation zone 300 is routed to mother liquor purge zone 700 wherein a portion of the impurities present in stream 330 are isolated and exit the process as purge stream 751. The portion of stream 330 going to the mother liquor purge zone 700 can be 5% by weight or greater, 25% by weight or greater, 45% by weight or greater, 65% by weight or greater, 85% by weight or greater, or 95% by weight or greater. Recycle oxidation solvent stream 711 comprises oxidation solvent isolated from stream 330 and can be recycled to the process. The raffinate stream 742 comprises oxidation catalyst isolated from stream 330 which can optionally be recycled to the process. In one embodiment, the raffinate stream 742 is recycled to oxidation zone 100 and contains greater than 30 wt %, greater than 50 wt %, greater than 80 wt %, or greater than 90 wt % of the catalyst that entered the mother liquor purge zone 700 in stream 330. In another embodiment, at least a portion of mother liquor stream 330 is routed directly to oxidation zone 100 without first being treated in mother liquor purge zone 700. In one embodiment, mother liquor purge zone 700 comprises an evaporative step to separate oxidation solvent from stream 330 by evaporation.

One embodiment of mother liquor purge zone 700 comprises routing at least a portion of oxidizer mother liquor stream 330 to solvent recovery zone 710 to generate a recycle oxidation solvent stream 711 comprising oxidation solvent and an impurity rich waste stream 712 comprising oxidation by products and catalyst. Any technology known in the art capable of separating a volatile solvent from stream 330 may be used. Examples of suitable unit operations include, but are not limited to, batch and continuous evaporation equipment operating above atmospheric pressure, at atmospheric pressure, or under vacuum. A single or multiple evaporative steps may be used. In an embodiment of the invention, sufficient oxidation solvent is evaporated from stream 330 to result in stream 712 being present as a slurry having a weight percent solids greater than 10 weight percent, 20 weight percent, 30 weight percent, 40 weight percent, or 50 weight percent. At least a portion of impurity rich stream 712 can be routed to catalyst recovery zone 760 to generate catalyst rich stream 761. Examples of suitable unit operations for catalyst recovery zone 760 include, but are not limited to, incineration or burning of the stream to recover noncombustible metal catalyst in stream 761.

Another embodiment of mother liquor purge zone 700 comprises routing at least a portion of mother liquor stream 330 to solvent recovery zone 710 to generate a recycle oxidation solvent stream 711 comprising oxidation solvent and an impurity rich waste stream 712 comprising oxidation by products and catalyst. Any technology known in the art capable of separating a volatile solvent from stream 330 may be used. Examples of suitable unit operations include but are not limited to batch and continuous evaporation equipment operating above atmospheric pressure, at atmospheric pressure, or under vacuum. A single or multiple evaporative steps may be used. Sufficient oxidation solvent is evaporated from stream 330 to result in impurity rich waste stream 712 being present as slurry with weight % solids greater than 5 weight percent, 10 weight percent, 20 weight percent, and 30 weight percent. At least a portion of the impurity rich waste stream 712 is routed to a solid liquid separation zone 720 to generate a purge mother liquor stream 723 and a wet cake stream 722 comprising impurities. In another embodiment of the invention, all of stream 712 is routed to the solid liquid separation zone 720. Stream 722 may be removed from the process as a waste stream. Wash stream 721 may also be routed to solid-liquid separation zone 720 which will result in wash liquor being present in stream 723. It should be noted that zone 720 is a separate and different zone from zone 300.

Any technology known in the art capable of separating solids from slurry may be used. Examples of suitable unit operations include, but are not limited to, batch or continuous filters, batch or continuous centrifuges, filter press, vacuum belt filter, vacuum drum filter, continuous pressure drum filter, candle filters, leaf filters, disc centrifuges, decanter centrifuges, basket centrifuges, and the like. A continuous pressure drum filter is a preferred device for solid-liquid separation zone 720.

Purge mother liquor stream 723 comprising catalyst and impurities, and stream 731 comprising a catalyst solvent are routed to mix zone 731 to allow sufficient mixing to generate extraction feed stream 732. In one embodiment, stream 731 comprises water. Mixing is allowed to occur for at least 30 seconds, 5 minutes, 15 minutes, 30 minutes, or 1 hour. Any technology know in the art may be used for this mixing operation including inline static mixers, continuous stirred tank, mixers, high shear in line mechanical mixers and the like.

Extraction feed stream 732, recycle extraction solvent stream 752, and fresh extraction solvent stream 753 are routed to liquid-liquid extraction zone 740 to generate an extract stream 741 comprising impurities and extract solvent, and a raffinate stream 742 comprising catalyst solvent and oxidation catalyst that can be recycled directly or indirectly to the oxidation zone 100. Liquid-liquid extraction zone 740 may be accomplished in a single or multiple extraction units. The extraction units can be batch and or continuous. An example of suitable equipment for extraction zone 740 includes multiple single stage extraction units. Another example of suitable equipment for extraction zone 740 is a single multi stage liquid-liquid continuous extraction column. Extract stream 741 is routed to distillation zone 750 where extraction solvent is isolated by evaporation and condensation to generate recycle extract solvent stream 752. The purge stream 751 is also generated and can be removed from the process as a waste purge stream. Batch or continuous distillation may be used in distillation zone 750.

In another embodiment, the source for oxidizer mother liquor stream 330 feeding mother liquor purge zone 700 may originate from any mother liquor stream comprising oxidation solvent, oxidation catalyst, and impurities generated in process to make furan-2,5-dicarboxylic acid (FDCA). For example, a solvent swap zone downstream of oxidation zone 100 that isolates at least a portion of the FDCA oxidation solvent from stream 110 can be a source for stream 330. Suitable equipment for a solvent swap zone comprises solid-liquid separation devices including centrifuges and filters. Examples of suitable equipment for the solvent swap include, but is not limited to, a disc stack centrifuge or a continuous pressure drum filter.

EXAMPLES

This invention can be further illustrated by the following examples of embodiments thereof, although it will be understood that these examples are included merely for the purposes of illustration and are not intended to limit the scope of the invention unless otherwise specifically indicated.

Air oxidation of 5-HMF/5-AMF/5-EMF using cobalt, manganese and ionic bromine catalysts system in acetic acid solvent were conducted. After reaction the heterogeneous mixture was filtered to isolate the crude FDCA. The crude FDCA was washed with acetic acid two times and then twice with DI water. The washed crude FDCA was oven dried at 110° C. under vacuum overnight. The solid and the filtrate were analyzed by Gas Chromatography using BSTFA derivatization method. b* of the solid was measured using a Hunter Ultrascan XE instrument. As shown in Tables 1 to 3 we have discovered conditions that to generate yields of FDCA up to 89.4%, b*<6, and low carbon burn (<0.00072 mol/min $CO+CO_2$)

TABLE 1

Results from semi-batch reactions using 5-HMF feed.*

| Note-Book No. | Example | Bromide source | Co conc (ppm) | Mn conc (ppm) | Br conc (ppm) | yield of FDCA (%) | yield of FFCA (%) | CO (total mol) | $CO_2$ (total mol) | $CO_x$ (mol/min) | color (b*) |
|---|---|---|---|---|---|---|---|---|---|---|---|
| Ex-000250-187 | 1a | solid NaBr | 2000 | 93.3 | 3000 | 81.6 | 0.81 | 0.013 | 0.078 | 0.000758 | 13.91 |
| Ex-000186-019 | 1b | solid NaBr | 2000 | 93.3 | 3000 | 82.6 | 0.87 | 0.013 | 0.092 | 0.000875 | 14.14 |
| Ex-000186-004 | 2a | aqueous HBr | 2000 | 93.3 | 3000 | 89.4 | 0.58 | 0.003 | 0.061 | 0.000533 | 5.845 |
| Ex-000186-016 | 2b | aqueous HBr | 2000 | 93.3 | 3000 | 88.6 | 0.8 | 0.0037 | 0.061 | 0.000539 | 6.175 |

*P = 130 psig, $CO_x$ (mol/min) = CO (mol/min) + CO2 (mol/min).

TABLE 2

Results from semi-batch reactions using 5-AMF feed.*

| Note Book # | Example | Co conc (ppmw) | Mn conc (ppmw) | Br conc (ppmw) | Temperature (° C.) | % yield of FDCA | % yield of FFCA | CO (total mol) | CO2 (total mol) | CO$_x$ (mol/min) | color (b*) |
|---|---|---|---|---|---|---|---|---|---|---|---|
| 186-026 | 2a | 2500 | 116.8 | 2500 | 130 | 88.2 | 0.25 | 0.0052 | 0.08 | 0.00071 | 4.4 |
| 186-044 | 2b | 2000 | 93.5 | 3000 | 130 | 90.2 | 0.16 | 0.005 | 0.046 | 0.000425 | 6.8 |

*P = 130 psig, CO$_x$ (mol/min) = CO (mol/min) + CO2 (mol/min).

TABLE 3

Results from semi-batch reactions using 5-EMF feed.*

| Note Book # | Example | Co conc (ppmw) | Mn conc (ppmw) | Br conc (ppmw) | Temperature (° C.) | % yield of FDCA | % yield of FFCA | % yield of EFCA | CO (total mol) | CO2 (total mol) | CO$_x$ (mol/min) | color (b*) |
|---|---|---|---|---|---|---|---|---|---|---|---|---|
| 186-028 | 3a | 2500 | 116.8 | 2500 | 130 | 88.8 | 0.02 | 0.225 | 0.008 | 0.068 | 0.00063333 | 3.97 |
| 186-031 | 3b | 2000 | 93.5 | 3000 | 130 | 88.0 | 0.09 | 0.43 | 0.008 | 0.078 | 0.00071667 | 2.48 |
| 186-034 | 3c | 2000 | 93.5 | 3000 | 105 | 86.0 | 2.92 | 1.4 | 0.005 | 0.046 | 0.000425 | 6.66 |
| 186-038 | 3d | 2500 | 116.8 | 2500 | 130 | 87.4 | 0.42 | 1.3 | 0.009 | 0.064 | 0.00060833 | 2.74 |

*P = 130 psig, CO$_x$ (mol/min) = CO (mol/min) + CO2 (mol/min).

CLAIMS NOT LIMITED TO DISCLOSED EMBODIMENTS

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

We claim:

1. A process to produce a raffinate stream in a method for making a carboxylic acid, said process comprising:
    (i) oxidizing in an oxidation zone an oxidizable raw material stream comprising 5-(hydroxymethyl) furfural (5-HMF) in the presence of an oxidation solvent stream comprising a saturated organic acid having from 2-4 carbon atoms and a catalyst at a temperature of 100° C. to 220° C. to produce a crude carboxylic acid slurry;
    wherein said oxidation zone comprises at least one oxidation reactor;
    wherein said crude carboxylic acid slurry comprises furandicarboxylic acid;
    wherein said catalyst comprises cobalt, manganese and bromine; and
    (ii) after said oxidizing routing said crude carboxylic acid slurry to a solid liquid separation zone that is operated at a temperature between about 100°C. to about 220°C. to produce a mother liquor stream comprising the catalyst and impurities;
    (iii) routing at least a portion of the mother liquor stream to a mother liquor purge zone comprising a mixing zone and a liquid-liquid extraction zone;
    (iv) mixing at least a portion of the mother liquid stream with a catalyst solvent in the mixing zone to generate an extraction feed stream; and
    (v) contacting the extraction feed stream with an extraction solvent stream in the liquid-liquid extraction zone to generate an extract stream comprising the impurities and the extraction solvent, and a raffinate stream comprising the catalyst and the catalyst solvent; wherein said oxidizable raw material stream comprises greater than 20% by weight of 5-HMF.

2. The process according to claim 1 wherein said catalyst comprises cobalt in a range from about 500 ppm by weight to about 6000 ppm by weight with respect to the weight of the liquid in the reaction medium, manganese in an amount ranging from about 2 ppm by weight to about 600 ppm by weight with respect to the weight of the liquid in the reaction medium, and bromine in an amount ranging from about 300 ppm by weight to about 4500 ppm by weight with respect to the weight of the liquid in the reaction medium.

3. The process according to claim 1 wherein said oxidation reactor is a bubble column.

4. The process according to claim 1 wherein said catalyst comprises cobalt in a range from about 700 ppm to about 4500 ppm by weight with respect to the weight of the liquid in the reaction medium, manganese in an amount ranging from about 20 ppm by weight to about 400 ppm by weight with respect to the weight of the liquid in the reaction medium, and bromine in an amount ranging from about 700 ppm by weight to about 4000 ppm by weight with respect to the weight of the liquid in the reaction medium.

5. The process according to claim 1 wherein said catalyst comprises cobalt in a range from about 1000 ppm to about 4000 ppm with respect to the weight of the liquid in the reaction medium, manganese in an amount ranging from about 20 ppm to about 200 ppm by weight with respect to the weight of the liquid in the reaction medium and bromine in an amount ranging from about 1000 ppm to about 4000 ppm by weight with respect to the weight of the liquid in the reaction medium.

6. The process according claim 1 wherein said crude carboxylic acid slurry further comprises 5-formyl furan-2-carboxylic acid (FFCA).

7. The process according to claim 1 wherein said oxidizing is conducted at a temperature from 105° C. to 180° C.

8. The process according to claim 1 wherein said oxidizing is conducted at a temperature from 110° C. to 160° C.

9. The process according to claim 1 wherein said oxidizable raw material stream comprises greater than 50% by weight of 5-HMF.

10. The process according to claim 1 wherein said oxidizable raw material stream comprises greater than 70% by weight of 5-HMF.

11. The process according to claim 1 wherein the weight ratio of cobalt to manganese is about 400 to about 1.

12. The process according to claim 1 wherein the weight ratio of cobalt to manganese is about 40 to about 1.

13. The process according to claim 1 wherein the weight ratio of cobalt to manganese is about 30 to about 1.

14. The process according to claim 1 wherein the weight ratio of cobalt to manganese is about 20 to about 1.

15. The process according to claim 1 wherein the weight ratio of cobalt to manganese is about 10 to about 1.

16. The process according to claim 11 wherein the weight ratio of cobalt to bromine is about 0.75 to about 3.5.

* * * * *